(12) United States Patent
Golan et al.

(10) Patent No.: US 11,553,936 B2
(45) Date of Patent: Jan. 17, 2023

(54) IMPACTOR AND STABILIZER FOR FRACTURING CALCIFICATIONS IN HEART VALVES

(71) Applicant: Pi-Cardia Ltd., Rehovot (IL)

(72) Inventors: Erez Golan, Rehovot (IL); Ofir Gal-Or, Gedera (IL); Oded Meiri, Ram-On (IL); Ronnie Levy, Kochav-Yair (IL); Shai Kami, Rehovot (IL)

(73) Assignee: Pi-Cardia Ltd., Rehovot (IL)

( * ) Notice: Subject to any disclaimer, the term of this patent is extended or adjusted under 35 U.S.C. 154(b) by 394 days.

(21) Appl. No.: 16/852,694

(22) Filed: Apr. 20, 2020

(65) Prior Publication Data

US 2020/0246030 A1    Aug. 6, 2020

Related U.S. Application Data

(63) Continuation of application No. 15/723,379, filed on Oct. 3, 2017, now Pat. No. 10,624,658.

(51) Int. Cl.
*A61B 17/221* (2006.01)
*A61B 17/3207* (2006.01)
(Continued)

(52) U.S. Cl.
CPC ...... *A61B 17/221* (2013.01); *A61B 17/22031* (2013.01); *A61B 17/3207* (2013.01); *A61B 2017/00836* (2013.01); *A61B 2017/00867* (2013.01); *A61B 2017/22038* (2013.01); *A61B 2017/22098* (2013.01)

(58) Field of Classification Search
CPC .......... A61B 2017/22098; A61B 2017/22038; A61B 2017/00867; A61B 2017/00836; A61B 17/3207; A61B 17/22031; A61B 17/221

See application file for complete search history.

(56) References Cited

U.S. PATENT DOCUMENTS

| 6,306,163 | B1 | 10/2001 | Fitz |
| 10,624,658 | B2* | 4/2020 | Golan ................ A61B 17/3207 |

(Continued)

FOREIGN PATENT DOCUMENTS

WO    2011/069025    6/2011

OTHER PUBLICATIONS

Japanese Patent Application 2020-517864 office action, dated Mar. 24, 2022.

*Primary Examiner* — Jocelin C Tanner
(74) *Attorney, Agent, or Firm* — Dekel Patent Ltd.; David Klein

(57) ABSTRACT

A device for fracturing calcifications in heart valves includes a stabilizer and an impactor movable towards each other. The impactor includes one or more impactor arms, each of which extends distally from a proximal cap. The impactor further includes one or more lever arms each of which is distally coupled to a lever cap and proximally coupled to a corresponding one of the one or more impactor arms. The lever cap slides on a shaft which extends towards the proximal cap. Proximal movement of the lever cap towards the proximal cap causes the one or more lever arms to deform and to push against the one or more impactor arms and to cause the one or more impactor arms to deform.

18 Claims, 2 Drawing Sheets

(51) Int. Cl.
    *A61B 17/22*     (2006.01)
    *A61B 17/00*     (2006.01)

(56) References Cited

U.S. PATENT DOCUMENTS

| | | | |
|---|---|---|---|
| 2012/0253358 A1* | 10/2012 | Golan | A61B 17/221 606/128 |
| 2014/0316428 A1* | 10/2014 | Golan | A61B 17/22031 606/128 |
| 2015/0335340 A1* | 11/2015 | Golan | A61B 17/00234 606/128 |

* cited by examiner

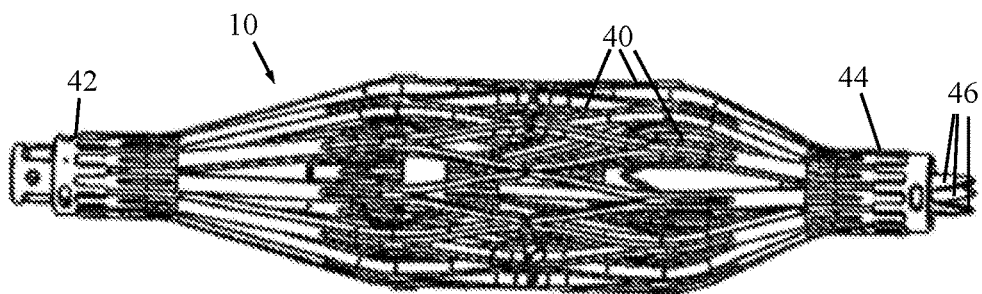
FIG. 6
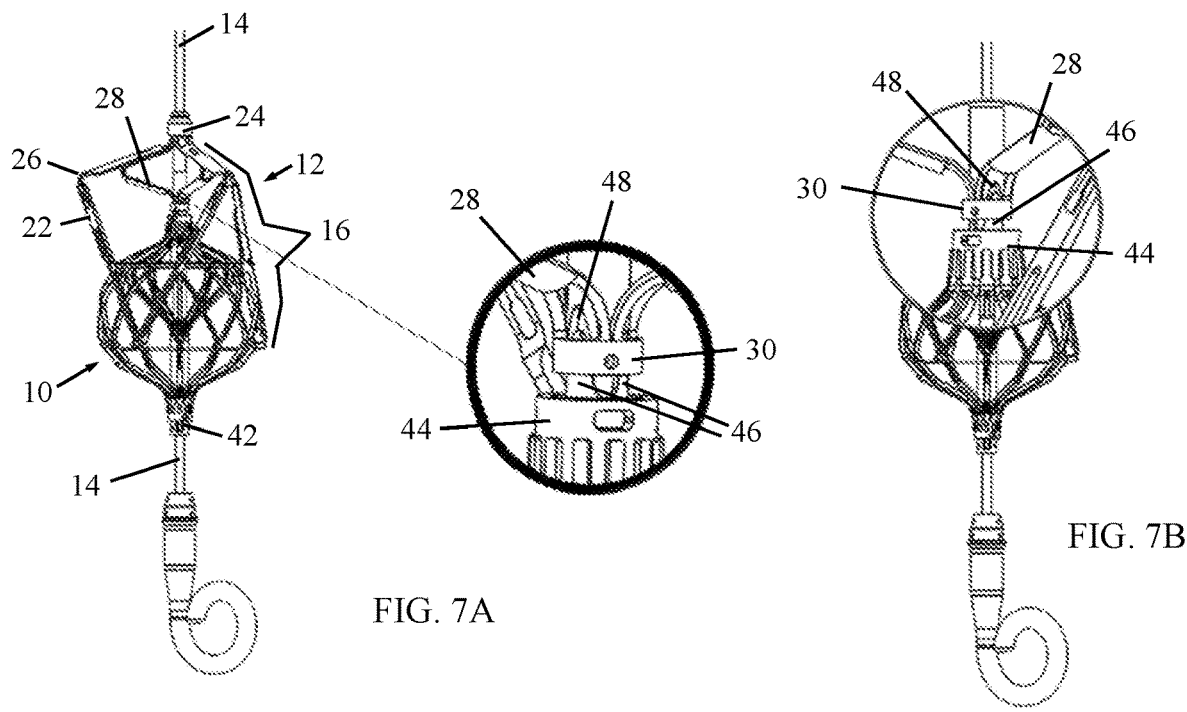
FIG. 7A
FIG. 7B
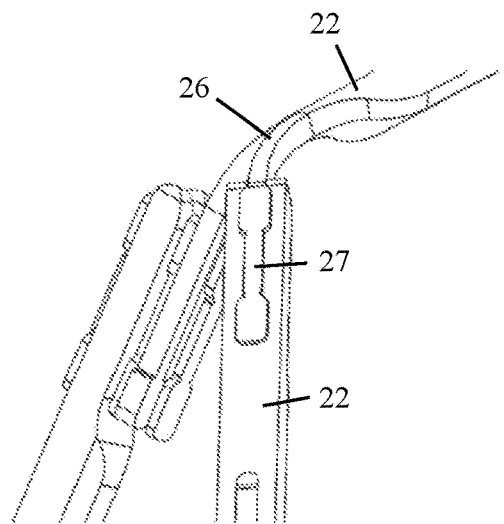
FIG. 8

IMPACTOR AND STABILIZER FOR FRACTURING CALCIFICATIONS IN HEART VALVES

FIELD OF THE INVENTION

The present invention generally relates to devices and methods for fracturing calcifications in heart valves, such as aortic valve leaflets.

BACKGROUND OF THE INVENTION

PCT Patent Applications PCT/US2010/058810 and PCT/US2012/067812, assigned to the present assignee, describe devices for fracturing calcifications in heart valves. The device includes a catheter that has an expandable stabilizer, an impactor shaft and an internal shaft, all disposed in an external shaft. Expandable impactor arms are mounted on the impactor shaft. The internal shaft is movable to cause the impactor arms to expand outwards and be locked in an expanded shape. An impacting element is movable to cause the impactor arms, while in the expanded shape, to move towards the tissue with sufficient energy so as to fracture a calcification located in tissue which is fixed by the stabilizer in a certain position vis-à-vis the impactor arms. The internal shaft may be lockable relative to the impactor shaft so that the impactor arms are fixed.

A brief description of using these prior art devices is as follows. The catheter may be delivered over a guide-wire through a blood vessel, such as the peripheral artery, using a retrograde approach, through the aortic arch and into the ascending aorta, just above the aortic valve. The external shaft is retracted so that the expandable stabilizer expands and opens up. The stabilizer is used to guide, position and anchor the catheter distal part in the sinuses, just above the valve leaflets. An impactor shaft, including folded impactor arms, is then pushed forward (distally) through the center of the valve into the left ventricle. When pushed forward the impactor arms are folded so that they can easily cross the valve. The internal shaft is then pulled proximally to cause the impactor arms to open (expand) outwards sideways and lock them in the expanded shape. The impactor and internal shafts are manipulated so that the leaflets are "sandwiched" between the stabilizer (which may make contact with the leaflets from the aortic aspect) and the impactor arms (which may make contact with the leaflets from the ventricular aspect, or vice versa). In order to fracture leaflet calcifications, the impactor arms are pulled abruptly towards the leaflet tissue to impact the calcification, with the stabilizer serving as an anvil.

SUMMARY OF THE INVENTION

The present invention seeks to provide further impactor devices that may be used for fracturing calcifications in aortic valve leaflets, in order to increase leaflet pliability and mobility, either as standalone treatment, bridge treatment or preparation of the "landing zone" for trans-catheter valve implantation.

The term "fracture" refers to any kind of reduction in size or any modification in shape or form, such as but not limited to, fracturing, pulverizing, breaking, grinding, chopping and the like.

There is provided in accordance with an embodiment of the invention a device for fracturing calcifications in heart valves including a stabilizer and an impactor movable towards each other, such as but not necessarily, on a guidewire, the impactor including one or more impactor arms, each of which extends distally from a proximal cap, the impactor further including one or more lever arms each of which is distally coupled to a lever cap and proximally coupled to a corresponding one of the one or more impactor arms, the lever cap being arranged for sliding on a shaft which extends towards the proximal cap, wherein proximal movement of the lever cap towards the proximal cap causes the one or more lever arms to deform and to push against the one or more impactor arms and to cause the one or more impactor arms to deform.

In accordance with a non-limiting embodiment of the invention each of the one or more lever arms is formed with a pivot.

In accordance with a non-limiting embodiment of the invention each of the one or more impactor arms includes an arm member formed with a pivot.

In accordance with a non-limiting embodiment of the invention a limiter is coupled to a (e.g., distal) portion of the one or more impactor arms, the limiter controlling an amount of radially-outward expansion of distal portions of the one or more impactor arms.

In accordance with a non-limiting embodiment of the invention when the one or more impactor arms deform by the proximal movement of the lever cap towards the proximal cap, distal portions of the one or more impactor arms do not expand radially outwards.

In accordance with a non-limiting embodiment of the invention the stabilizer includes mating structure for engagement with the impactor.

In accordance with a non-limiting embodiment of the invention the mating structure includes registration lugs that protrude proximally from a proximal end piece of the stabilizer, the registration lugs being arranged to move into grooves formed in the one or more lever arms.

In accordance with a non-limiting embodiment of the invention each of the one or more impactor arms includes struts which meet at a rounded junction.

BRIEF DESCRIPTION OF THE DRAWINGS

The present invention will be understood and appreciated more fully from the following detailed description, taken in conjunction with the drawings in which:

FIG. 6 is a simplified pictorial illustration of the stabilizer, showing mating structure for engagement with the impactor;

FIGS. 7A and 7B are simplified enlarged illustrations of engagement of the stabilizer with the impactor, showing how the mating structure registers the stabilizer with respect to the impactor; and FIG. 8 is a simplified enlarged illustration of structure of the impactor arms of the impactor, in one non-limiting embodiment of the invention.

DETAILED DESCRIPTION OF EMBODIMENTS

First an overall description of the stabilizer and impactor of the invention and one possible delivery are described with reference to FIGS. 1-4. A more detailed description of the stabilizer and impactor then follows with reference to FIGS. 5A-6.

Reference is now made to FIGS. 1-4, which illustrates a stabilizer 10 and an impactor 12, which may be delivered over a guidewire 14 (such as with a delivery catheter, not shown), in accordance with a non-limiting embodiment of the invention.

Guidewire 14 is first moved through a blood vessel, such as a peripheral artery, using a retrograde approach, through the aortic arch and into the ascending aorta, and then through the aortic valve into the left ventricle. The delivery catheter is then moved over the guidewire 14 and delivers stabilizer 10 through the ascending aorta into the aortic root and through the aortic annulus into the left ventricle, inferior to the aortic valve. The impactor 12 may be delivered over the same guidewire 14 through the ascending aorta and then through the sinotubular junction into the Valsalva sinuses of the aortic root, just above the cusps of the aortic valve, so that the impactor 12 is superior to the leaflets and the stabilizer 10 is inferior to the leaflets (the positions in FIGS. 2-4).

Figure 1:
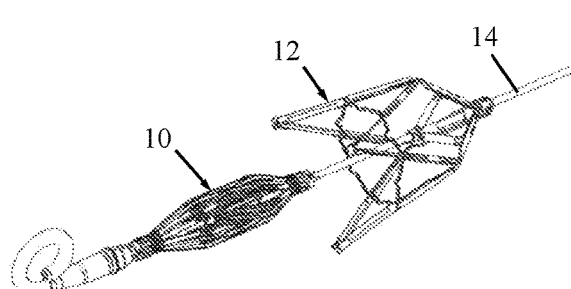
FIG. 1 is a simplified pictorial illustration of a stabilizer and an impactor, delivered over a guidewire, in accordance with a non-limiting embodiment of the invention.
Figure 2:
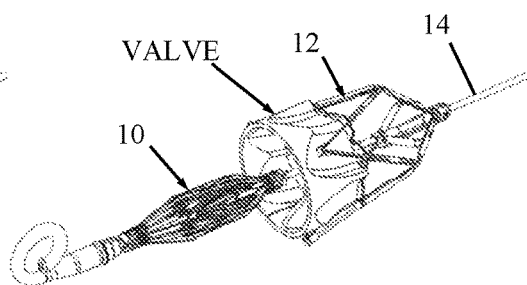
FIG. 2 is a simplified pictorial illustration of the impactor positioned over leaflets of a valve, such as the aortic valve, in which case the stabilizer has first been delivered in a retrograde delivery through the ascending aorta into the aortic root and through the aortic annulus into the left ventricle, and the impactor has been delivered over the same guidewire through the ascending aorta into the aortic root, so that the stabilizer is inferior to the leaflets and the impactor is superior to the leaflets.
Figure 3:
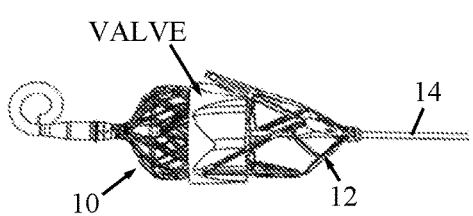
FIG. 3 is a simplified pictorial illustration of moving the stabilizer and the impactor towards each other, the leaflets being sandwiched between the stabilizer and the impactor.

In FIG. 3, the stabilizer 10 and impactor 12 are moved towards each other. For example, stabilizer 10 may be moved proximally towards impactor 12; impactor 12 may be moved distally towards stabilizer 10; or stabilizer 10 may be moved proximally towards impactor 12 and impactor 12 may be moved distally towards stabilizer 10. In all cases, the leaflets are sandwiched between stabilizer 10 and impactor 12.

Figure 4:
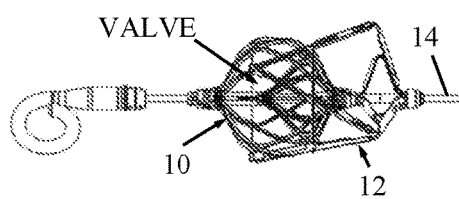
FIG. 4 is a simplified pictorial illustration of expanding the stabilizer which acts to deploy the impactor arms of the impactor.

In FIG. 4, stabilizer 10 is expanded, which acts to deploy impactor arms of impactor 12. The movement of stabilizer 10 and impactor 12 towards each other fractures leaflet calcifications. After fracturing leaflet calcifications, the stabilizer 10 and impactor 12 may be removed by moving them proximally over guidewire 14 and then removing guidewire 14.

Figure 5A:
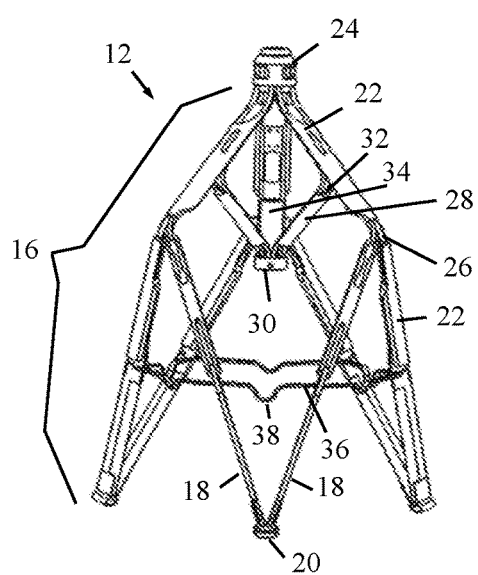
FIGS. 5A and 5B are simplified pictorial illustrations of the impactor, respectively, before and after expansion (that is, respectively in contracted and expanded orientations)
Figure 5B:
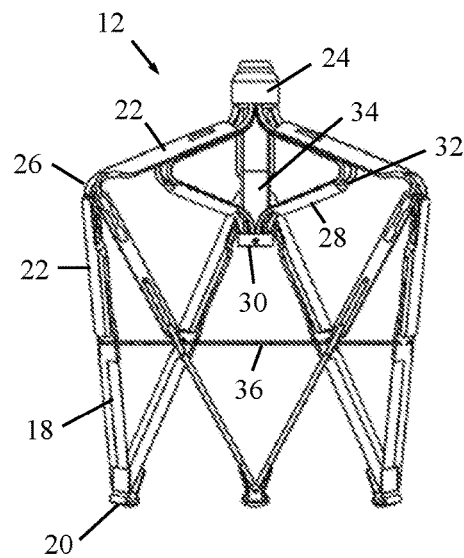

Reference is now made to FIGS. 5A and 5B, which illustrate the impactor 12, in accordance with a non-limiting embodiment of the invention.

Impactor 12 includes one or more impactor arms 16. In the illustrated embodiment there are three impactor arms 16, which are suitable for a tricuspid valve, but the invention may be carried out with other numbers of arms. Each arm 16 may be constructed of two struts 18 which meet at a junction 20, such as a rounded end cap, which may be secured to the struts 18, such as but not limited to, by welding, brazing, bonding or other joining techniques, or may be one piece with the struts. The roundness of junction 20 may help prevent piercing tissue during operation of the device.

Each strut 18 may include a slender member, such as but not limited to, a wire, rod, strip, thin beam and the like, coupled to an arm member 22. Arm member 22 extends from the proximal end of strut 18 to a proximal cap 24, and is formed with a pivot 26 intermediate the proximal end of strut 18 and the proximal cap 24. Pivot 26 may be a score line, thinner portion, weakened portion and the like, which enables arm member 24 to bend or buckle when being expanded from the contracted orientation to the expanded orientation. FIG. 8 illustrates one possible structure of pivot 26, in which the proximal portion of the arm member 22 has a thinner portion which serves as pivot 26, and terminates in a flap 27 which is welded or otherwise joined to the distal portion of arm member 22. Of course, the arm member 22 may be a one-piece construction or other constructions. It is noted that arm member 22 may be of sufficient length and stiffness to that it itself is the strut (and ends at junction 20) and there is no need to couple a strut to the arm member.

Impactor 12 includes one or more lever arms 28. In the illustrated embodiment there are three lever arms 28, but the invention may be carried out with other numbers of lever arms; there is preferably a one-to-one correspondence of lever arms 28 to arm members 22. The distal ends of the lever arms 28 may be coupled to a lever cap 30 and each of the proximal ends of the lever arms 28 may be coupled to a proximal portion of a corresponding arm member 22. Each lever arm 28 is formed with a pivot 32 intermediate the proximal and distal ends of lever arm 28. Pivot 32 may be a score line, thinner portion, weakened portion and the like, which enables lever arm 28 to bend or buckle during expansion. Lever cap 30 may be arranged for sliding on a shaft 34 (which may be telescoping) which extends towards proximal cap 24 (either reaching or not reaching proximal cap 24). It is noted that the impactor arms 16 and the lever arms 28 may deform (without limitation, bend, bow or buckle, etc.) outwards even without pivots, due to their elasticity or flexibility. The pivots may help define the place where they bend, bow or buckle.

A limiter 36 may be coupled to a (e.g., distal) portion of arm members 22, such as by being assembled in mounting holes or any other suitable method. The limiter 36, as well as any other part of the device (both impactor and stabilizer) may be made from nitinol or stainless steel or any other suitable material.

FIG. 5A illustrates impactor 12 in the contracted orientation. In order to expand impactor arms 16 to the expanded orientation of FIG. 5B, lever cap 30 is moved proximally towards proximal cap 24, which causes lever arms 28 to deform, e.g., bend or buckle radially outwards at pivots 32. The outward movement of the proximal portions of lever arms 28 pushes the proximal portions of arm members 22 outwards and proximally (upwards in the sense of FIGS. 5A and 5B), and the arm members 22 deform, e.g., bend or buckle at pivot 26. Although in one embodiment the distal portions of arm members 22 may expand radially outwards, in the preferred embodiment the distal portions of arm members 22 do not expand radially outwards but rather either remain at approximately the same radial position or contract radially inwards. The amount of radially-outward expansion of the distal portions of arm members 22 is controlled by the limiter 36. Limiter 36 may be formed with an intermediate bend 38, which stretches and straightens when impactor arms 16 are expanded.

Reference is now made to FIG. 6, which illustrates the stabilizer 10. Stabilizer 10 may be formed with a plurality of flexible members 40, which may form a web, mesh truss or similar structure, which can be expanded outwards. The distal ends of flexible members 40 may be coupled to a distal end piece 42 and the proximal ends of flexible members 40 may be coupled to a proximal end piece 44. Stabilizer 10 may be formed with a plurality of registration lugs 46, such as resilient fingers that protrude proximally from proximal end piece 44. The proximal end piece 44 and the registration lugs 46 together form mating structure for engagement with the impactor 12, as is now explained with reference to the enlarged views of FIGS. 7A and 7B.

In FIG. 7A, stabilizer 10 and impactor 12 have been moved towards each other. The registration lugs 46 that protrude proximally from proximal end piece 44 pass through an inner radial gap in lever cap 30 of lever arms 28 and are received in grooves 48 formed in the distal portions of lever arms 28. The groove 48 may be any kind of cutout, either through the entire thickness of the lever arm or not through the entire thickness (i.e., blind), such as but not limited to, a notch, aperture, depression, channel and the like.

The stabilizer 10 (via the engagement of registration lugs 46 with lever cap 30) causes lever cap 30 to move proximally towards proximal cap 24, which causes lever arms 28 to bend or buckle radially outwards and pushes the proximal portions of arm members 22 outwards and proximally. Arm members 22 bend or buckle at pivot 26. The impactor 12 is now ready to fracture calcifications in the leaflets.

The registration lugs 46 and the grooves 48 may self-align, that is, the registration lugs 46 may circumferentially rotate somewhat as they slide into grooves 48. The registration of registration lugs 46 with grooves 48 may help achieve proper registration of the impactor arms 16 with the leaflets of the valve so that the impactor arms 16 are properly positioned over the calcifications in order to fracture them.

The term "fracture" refers to any kind of reduction in size or any modification in shape or form, such as but not limited to, fracturing, pulverizing, scoring, breaking, grinding, chopping and the like.

What is claimed is:

1. A device for fracturing calcifications in a heart valve, the device comprising:
    a stabilizer; and
    an impactor movable towards the stabilizer, the impactor comprising a cap and one or more impactor arms that extend distally from the cap, the cap configured to slide on a shaft of the device, the one or more impactor arms each formed with a pivot,
    wherein the one or more impactor arms are configured to bend at the pivot as the impactor transitions from a contracted orientation to an expanded orientation to fracture calcifications at the heart valve between the impactor and the stabilizer, and further comprising one or more lever arms, each of the one or more lever arms proximally coupled to a corresponding impactor arm of the one or more impactor arms and distally coupled to a lever cap, the lever cap configured to slide on the shaft of the device relative to the cap.

2. The device of claim 1, wherein the stabilizer is configured to transition from a contracted orientation to an expanded orientation.

3. The device of claim 1, wherein the stabilizer comprises a distal end piece and a plurality of flexible members that extend from the distal end piece.

4. The device of claim 1, wherein the stabilizer comprises a mating structure for engagement with the impactor.

5. The device of claim 1, wherein the impactor is moveably towards the stabilizer such that one or more calcified leaflets of the heart valve are sandwiched between the stabilizer and the impactor.

6. The device of claim 1, wherein each of the one or more impactor arms comprises struts which meet at a rounded junction.

7. The device of claim 1, wherein distal portions of the one or more impactor arms remain at a constant radial position as the impactor transitions from the contracted orientation to the expanded orientation.

8. The device of claim 1, wherein distal portions of the one or more impactor arms contract radially inward as the impactor transitions from the contracted orientation to the expanded orientation.

9. The device of claim 1, wherein distal portions of the one or more impactor arms expand radially outward as the impactor transitions from the contracted orientation to the expanded orientation.

10. The device of claim 1, wherein each of the one or more lever arms is formed with a pivot.

11. The device of claim 10, wherein the pivot of the one or more lever arms is formed between a proximal end and a distal end of the one or more lever arms.

12. The device of claim 10, wherein the pivot comprises at least one of a score line, a thinner portion, or a weakened portion of the one or more lever arms.

13. The device of claim 1, wherein movement of the lever cap proximally toward the cap is configured to cause the one or more lever arms to push against the one or more impactor arms to transition the one or more impactor arms from the contracted orientation to the expanded orientation.

14. The device of claim 1, further comprising a limiter coupled to a distal portion of the one or more impactor arms, the limiter configured to control an amount of radially-outward expansion of the distal portion of the one or more impactor arms.

15. A method for fracturing calcifications in heart valves, the method comprising:
    advancing a stabilizer and an impactor to a calcified heart valve;
    moving the impactor relative to the stabilizer to position one or more calcified leaflets of the calcified heart valve between the impactor and the stabilizer;
    transitioning the impactor from a contracted orientation to an expanded orientation such that one or more impactor arms of the impactor bend at respective pivots of the one or more impactor arms; and
    fracturing the one or more calcified leaflets of the calcified heart valve between the stabilizer and the one or more impactor arms in the expanded orientation; and
    wherein transitioning the impactor from the contracted orientation to the expanded orientation comprises moving a lever cap proximally toward a proximal end of the impactor, the lever cap coupled to one or more lever arms extending from the lever cap to a corresponding impactor arm one of the one or more impactor arms, such that movement of the contracted orientation to the expanded orientation.

16. The method of claim 15, wherein advancing the stabilizer and the impactor to the calcified heart valve comprises advancing the stabilizer and the impactor to a calcified aortic valve.

17. The method of claim 15, wherein advancing the stabilizer and the impactor to the calcified heart valve comprises advancing the stabilizer and the impactor to a calcified tricuspid valve.

18. The method of claim 15, transitioning the stabilizer from a contracted orientation to an expanded orientation.

* * * * *